United States Patent [19]

Conrad et al.

[11] 4,124,541
[45] Nov. 7, 1978

[54] DIOXA BICYCLO DODECANE AND -HEXADECANE PERFUME COMPOSITIONS

[75] Inventors: Jens Conrad, Hilden; Ulf-Armin Schaper, Dusseldorf; Klaus Bruns, Krefeld, all of Germany

[73] Assignee: Henkel Kommanditgesellschaft auf Aktien, Dusseldorf-Holthausen, Germany

[21] Appl. No.: 806,616

[22] Filed: Jun. 15, 1977

[30] Foreign Application Priority Data

Jun. 28, 1976 [DE] Fed. Rep. of Germany ....... 2629000

[51] Int. Cl.² .............................................. C11B 9/00
[52] U.S. Cl. .................................. 252/522; 260/340.3; 424/358; 252/108; 252/174; 252/8.6; 252/89 R
[58] Field of Search ....................... 252/522; 260/340.3

[56] References Cited

U.S. PATENT DOCUMENTS

| | | | |
|---|---|---|---|
| 2,769,014 | 10/1956 | Beets | 252/522 |
| 3,326,746 | 6/1967 | Cahn et al. | 252/522 |
| 3,423,430 | 1/1969 | Cahn et al. | 252/522 |
| 3,801,600 | 4/1974 | Naegli | 252/522 |
| 3,840,559 | 8/1974 | Hoffmann | 252/522 |
| 3,884,841 | 5/1975 | Maessea et al. | 252/522 |
| 3,952,016 | 4/1976 | Barillo et al. | 252/522 |
| 3,966,647 | 6/1976 | Lamberti et al. | 252/522 |

FOREIGN PATENT DOCUMENTS 981,285  1/1965  United Kingdom ..................... 252/522

*Primary Examiner*—Veronica O'Keefe
*Attorney, Agent, or Firm*—Hammond & Littell

[57] ABSTRACT

A perfumery composition consisting essentially of from 1% to 50% by weight of an alkyl-substituted 1,4-dioxane of the formula

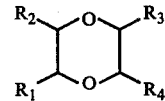

wherein $R_1$ is alkyl having from 4 to 12 carbon atoms, $R_2$ is hydrogen, $R_1$ and $R_2$, when taken together, represent a bivalent radical selected from the group consisting of alkylene having from 3 to 12 carbon atoms and alkylalkylene having from 1 to 4 carbon atoms in the alkyl and from 3 to 12 carbon atoms in the alkylene, $R_3$ and $R_4$ are individually members selected from the group consisting of hydrogen and alkyl having from 1 to 4 carbon atoms, and the remainder customary constituents of perfumery compositions, as well as novel 1,4-dioxanes of the above formula where either $R_3$ or $R_4$ or both are alkyl, or where $R_1$ and $R_2$, taken together, are a bivalent radical.

14 Claims, No Drawings

DIOXA BICYCLO DODECANE AND -HEXADECANE PERFUME COMPOSITIONS

BACKGROUND OF THE INVENTION

The present invention relates to perfumery composition containing alkyl-substituted 1,4-dioxanes and to some novel alkyl-substituted 1,4-dioxanes.

OBJECTS OF THE INVENTION

An object of the present invention is the development of perfumery compositions with characteristic fragrances and excellent adhesion.

Another object of the present invention is the development of a perfumery composition consisting essentially of from 1% to 50% by weight of an alkyl-substituted 1,4-dioxane of the formula

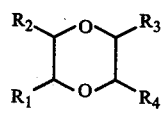

wherein $R_1$ is alkyl having from 4 to 12 carbon atoms, $R_2$ is hydrogen, $R_1$ and $R_2$, when taken together, represent a bivalent radical selected from the group consisting of alkylene having from 3 to 12 carbon atoms and alkylalkylene having from 1 to 4 carbon atoms in the alkyl and from 3 to 12 carbon atoms in the alkylene, $R_3$ and $R_4$ are individually members selected from the group consisting of hydrogen and alkyl having from 1 to 4 carbon atoms, and the remainder customary constituents of perfumery compositions.

A yet further object of the present invention is the obtaining of an alkyl substituted 1,4-dioxane of the formula

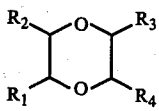

wherein $R_1$ is alkyl having from 4 to 12 carbon atoms, $R_2$ is hydrogen, $R_1$ and $R_2$, when taken together, represent a bivalent radical selected from the group consisting of alkylene having from 3 to 12 carbon atoms and alkylalkylene having from 1 to 4 carbon atoms in the alkyl and from 3 to 12 carbon atoms in the alkylene, $R_3$ and $R_4$ are individually members selected from the group consisting of hydrogen and alkyl having from 1 to 4 carbon atoms, with the proviso that when $R_1$ is said alkyl and $R_2$ is hydrogen, at least one of $R_3$ and $R_4$ is alkyl having from 1 to 4 carbon atoms.

These and other objects of the present invention will become more apparent as the description thereof proceeds.

DESCRIPTION OF THE INVENTION

It has been now found that alkyl-substituted 1,4-dioxanes of the following formula

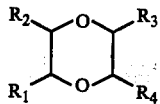

in which $R_1$ represents an alkyl having 4 to 12 carbon atoms, $R_2$ represents hydrogen or $R_1$ may be ring-closed with $R_2$ to form an optionally alkyl-substituted cycloalkyl radical which has 3 to 12 carbon atoms in the ring and $R_3$ and $R_4$ are the same or different and represent hydrogen or an alkyl group having 1 to 4 carbon atoms, particularly a methyl radical, can be used in an advantageous manner as perfumes having an intensive and adhering fragrance.

More particularly, the invention relates to a perfumery composition consisting essentially of from 1% to 50% by weight of an alkyl-substituted 1,4-dioxane of the formula

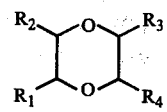

wherein $R_1$ is alkyl having from 4 to 12 carbon atoms, $R_2$ is hydrogen, $R_1$ and $R_2$, when taken together, represent a bivalent radical selected from the group consisting of alkylene having from 3 to 12 carbon atoms and alkylalkylene having from 1 to 4 carbon atoms in the alkyl and from 3 to 12 carbon atoms in the alkylene, $R_3$ and $R_4$ are individually members selected from the group consisting of hydrogen and alkyl having from 1 to 4 carbon atoms, and the remainder, customary constituents of perfumery compositions.

The dialkylated dioxanes and the bicyclo compounds are novel products. These are particularly alkyl-substituted 1,4-dioxanes of the formula

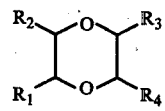

wherein $R_1$ is alkyl having from 4 to 12 carbon atoms, $R_2$ is hydrogen, $R_1$ and $R_2$, when taken together, represent a bivalent radical selected from the group consisting of alkylene having from 3 to 12 carbon atoms and alkylalkylene having from 1 to 4 carbon atoms in the alkyl and from 3 to 12 carbon atoms in the alkylene, $R_3$ and $R_4$ are individually members selected from the group consisting of hydrogen and alkyl having from 1 to 4 carbon atoms, with the proviso that when $R_1$ is said alkyl and $R_2$ is hydrogen, at least one of $R_3$ and $R_4$ is alkyl having from 1 to 4 carbon atoms.

The alkyl-substituted 1,4-dioxanes to be used, in accordance with the invention, as perfumes are produced by known methods. The production of the 1,4-dioxanes is based on terminal alkyl epoxides or cycloalkyl epoxides on the one hand and, on the other hand, 1,2-alkylene glycols, production being effected in two stages. In the first stage, the glycol is added to the epoxide in a reaction in the presence of an acid or alkaline catalyst according to the following reaction scheme:

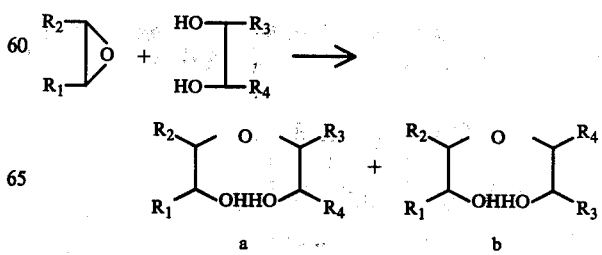

-continued

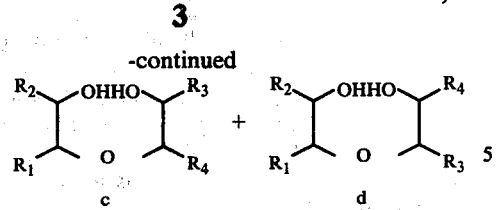

c          d

Several isomeric ether diols a to d can thus be produced by the reaction.

In the second stage, the dioxane ring is closed under acid catalysis with p-toluene sulfonic acid with the elimination of water. The water produced is distilled off azeotropically in a known manner by means of an azeotropic agent.

When using, for example, 1,2-propane diol ($R_3$ = $CH_3$, $R_4$ = H) and open-chain epoxides ($R_1$ = alkyl, $R_2$ = H), the ether diol b is produced as the main product with basic catalysis, since, in the first instance, the sodium reacts with the primary hydroxyl group of the 1,2-propane diol to form the corresponding alcoholate (see Houben-Weyl 6/2 10 (1963)), and the latter acts preferably on the end position $CH_2$ group of the epoxide (see Houben-Weyl 6/3 40 (1965)). The reaction can be carried out with molar or with catalytic quantities of sodium.

The acid catalysis reaction of the first stage is preferably carried out with boron trifluoride.

If different substituents $R_1$ to $R_4$ are present, several dioxane isomers can again be formed during the acid catalyzed ring closure reaction according to the following reaction scheme.

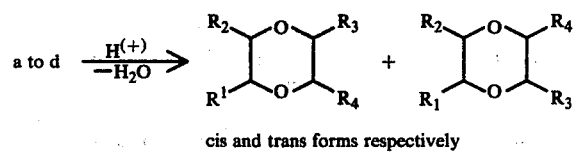

cis and trans forms respectively

The following 4 products appear when $R_1$ = $C_4$–$C_{12}$, $R_2$ = H, $R_3$ = $CH_3$, $R_4$ = H:

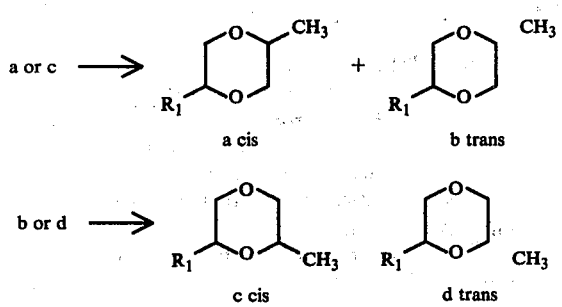

a cis          b trans c cis          d trans

The following four stereoisomers can appear when $R_1$ = $C_4$–$C_{12}$, $R_2$ = H, $R_3$ and $R_4$ = $CH_3$:

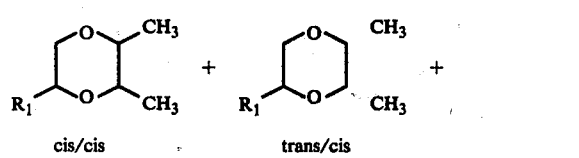

cis/cis          trans/cis

-continued

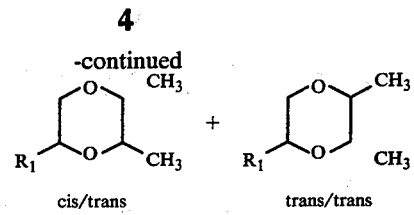

cis/trans          trans/trans

The isomers produced are not separated in any case, but are used in a mixed form as perfumes in all cases.

As stated above, the various modes of reaction of the first stage result in different isomer compositions of the end products. Thus, for example, the dioxanes cyclized by basic addition of 1,2-propane diol to long chain α-epoxides and by subsequent dehydration, generally have a more interesting odor than the products produced by acid catalysis. The description of the odors of alkaline and acid catalyzed reaction products are given separately in the Examples.

Alkyl-substituted 1,4-dioxanes to be used in accordance with the invention are, for example, 2-butyl-1,4-dioxane, 2-hexyl-1,4-dioxane, 2-octyl-1,4-dioxane, 2-decyl-1,4-dioxane, 2-dodecyl-1,4-dioxane, as well as the novel compounds which generally have the more interesting odors, such as 2-butyl-5, 6-dimethyl-1,4-dioxane, 2-hexyl-5,6-dimethyl-1,4-dioxane, 2-octyl-5,6-dimethyl-1,4-dioxane, 2-decyl-5,6-dimethyl-1,4-dioxane, 2-butyl-5,6-diethyl-1,4-dioxane, 2-butyl-5,6-dipropyl-1,4-dioxane, 2-hexyl-5,6-dibutyl-1,4-dioxane, a mixture of 2-butyl-6-methyl-1,4-dioxane and 2-butyl-5-methyl-1,4-dioxane, a mixture of 2-hexyl-6-methyl-1,4-dioxane and 2-hexyl-5-methyl-1,4-dioxane, a mixture of 2-octyl-6-methyl-1,4-dioxane and 2-octyl-5-methyl-1,4-dioxane, a mixture of 2-decyl-6-methyl-1,4-dioxane and 2-decyl-5-methyl-1,4-dioxane, a mixture of 2-butyl-6-ethyl-1,4-dioxane and 2-butyl-5-ethyl-1,4-dioxane, a mixture of 2-octyl-6-ethyl-1,4-dioxane and 2-octyl-5-ethyl-1,4-dioxane, a mixture of 2-decyl-6-ethyl-1,4-dioxane and 2-decyl-5-ethyl-1,4-dixoane, a mixture of 2-hexyl-6-butyl-1,4-dioxane and 2-hexyl-5-butyl-1,4-dioxane, 10-methyl-9,12-dioxa-bicyclo-(6,4,0)-dodecane, 9,12-dioxa-bicyclo-(6,4,0)-dodecane, 13,16-dioxa-bicyclo-(10,4,0)-hexadecane, 10,11-dimethyl-9,12-dioxa-bicyclo-(6,4,0)-dodecane, 14-methyl-13,16-dioxa-bicyclo-(10,4,0)-hexadecane, 14,15-dimethyl-13,16-dioxa-bicyclo-(10,4,0)-hexadecane.

The alkyl-substituted 1,4-dioxanes to be used in accordance with the present invention are valuable perfumes having characteristic fragrances. They are particularly distinguished by excellent adhesion. A further advantage is that they can be very satisfactorily combined to form novel fragrances of perfumery compositions in accordance with the present invention.

1,4-dioxanes, substituted in the 2nd position by longer chain alkyl radicals, have already been described in various references such as Nature 198, 284 (1963), J. Org. Chem. 29, 2031 (1964), Monatsh. Chemie 102, 114 (1971). However, no data is given concerning their perfume properties nor is there any suggestion given as to the possibility of using them as perfumes.

The alkyl-substituted 1,4-dioxanes to be used in accordance with the invention, as perfumes, can be mixed with other perfumes in a wide range of quantity ratios to form novel perfumery compositions. However, in general, the proportion of the alkyl-substituted 1,4-dioxanes to be used, in accordance with the invention, in the perfumery compositions will vary from 1% to 50% by weight relative to the total composition. The remainder of the composition is conventional perfumery constituents. Such a composition can act directly as a perfume or, alternatively, can be used to perfume cosmetics such as creams, lotions, toilet waters, aerosols, mouth washes, toilet soaps, etc. Alternatively, however, as is possible with some of the alkyl-substituted 1,4-dioxanes to be used in accordance with the invention, they can also be used to improve the odor of technical products such as washing and cleaning agents, disinfectants, agents for treating textiles, etc.

The following Examples are intended to further explain the subject of the invention, but without limiting the invention to these Examples.

EXAMPLES

The method of producing the alkyl-substituted 1,4-dioxanes given hereinafter will be described in the first instance.

(a) Production of ether diol by acid catalysis 0.5 mol of the particular epoxide, 0.75 mol of the particular 1,2-diol and 1.5 ml of boron trifluoride etherate were heated to 100° C. and were agitated for 15 to 20 hours at this temperature. After cooling, the mixture was dissolved in ether, washed neutral with water, dried over sodium sulfate, and recovered by distillation of the solvent in vacuo. The raw yield of ether diol was approximately 90% of theory. The raw ether diols can be purified by distillation in vacuo. Partial decomposition occurs, and a large residue was obtained. The yield was thereby reduced to approximately 40% of theory.

(b) Production of the ether diol by alkaline catalysis 1.5 g of sodium was dissolved in 1 mol of the particular diol. 0.25 mol of the particular epoxide was added thereto and the reaction mixture was heated to 180° C. for 6 to 8 hours. The surplus diol was distilled off in vacuo and the residue was added to 100 ml of 10% sulfuric acid. The oil which was precipitated was separated, and the aqueous phase was extracted three times with ether. The combined organic phases were washed neutral with water, dried and the product was recovered by distillation of the solvent in vacuo. The raw yield of ether diol was approximately 90% of theory.

(c) Production of the alkyl-substituted 1,4-dioxanes

The raw ether diol, produced as described above, was dissolved in xylene, p-toluene sulfonic acid was added, and the mixture was heated to boiling with azeotropic distillation for several hours to eliminate water.

When the formation of water had been concluded, the reaction mixture was cooled, washed neutral with water, dried over sodium sulfate, the solvent distilled in vacuo, and the product was distilled. The yield was approximately 80% of theory relative to the epoxide used.

All the alkyl-substituted 1,4-dioxanes give hereinafter were produced by the method described above. They constitute colorless oils or colorless solid products.

EXAMPLE 1

2-butyl-1,4-dioxane b.p.$_{20}$ 76° C. n$_D^{20}$ 1.4309

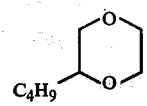

Odor: fruity, leathery, fragrance of potato plants.

EXAMPLE 2

2-hexyl-1,4-dioxane b.p.$_{0.2}$ 42° C. n$_D^{20}$ 1.4398

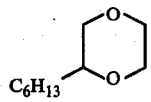

Odor: mushroom-like, earthy

EXAMPLE 3

2-octyl-1,4-dioxane b.p.$_{0.4}$ 96° C. f.p. 35°

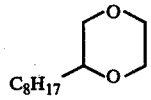

Odor: phenol, fatty alcohol fragrance

EXAMPLE 4

2-decyl-1,4-dioxane b.p.$_{0.2}$ 113° C. f.p. 45°

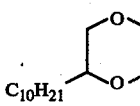

Odor: fatty alcohol fragrance

EXAMPLE 5

2-butyl-5,6-dimethyl-1,4-dioxane b.p.$_{0.2}$ 39° C. n$_D^{20}$ 1.432

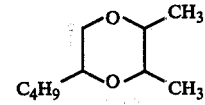

Odor: fruity, fragrance of milk

EXAMPLE 6

2-hexyl-5,6-dimethyl-1,4-dioxane b.p.$_{0.2}$ 65° C. n$_D^{20}$ 1.4376

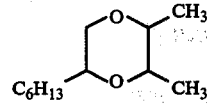

Odor: phenol, lovage fragrance

EXAMPLE 7

2-octyl-5,6-dimethyl-1,4-dioxane b.p.$_{0.2}$ 93° C. n$_D^{20}$ 1.4467

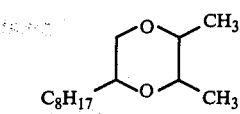

Odor: characteristic, cannot be further defined

EXAMPLE 8

2-decyl-5,6-dimethyl-1,4-dioxane b.p.$_{0.1}$ 105° C. n$_D^{20}$ 1.4478

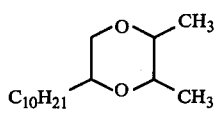

Odor: characteristic, cannot be further defined

EXAMPLE 9

Mixture of 2-butyl-6-methyl-1,4-dioxane and 2-butyl-5-methyl-1,4-dioxane b.p.$_{16}$ 80° C. n$_D^{20}$ 1.431

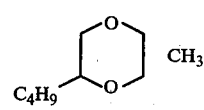

Odor: fresh, bonbon, catechu fragrance

EXAMPLE 10

Mixture of 2-hexyl-6-methyl-1,4-dioxane and 2-hexyl-5-methyl-1,4-dioxane b.p.$_{0.2}$ 54° C. n$_D^{20}$ 1.438

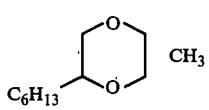

Odor: fatty, helional fragrance, cortex-cyclamal fragrance (alkaline preparation) flowery, fresh, straw-like (acid preparation)

EXAMPLE 11

Mixture of 2-octyl-6-methyl-1,4-dioxane and 2-octyl-5-methyl-1,4-dioxane b.p.$_{0.1}$ 76° C. n$_D^{20}$ 1.443

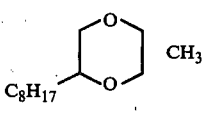

Odor: flowery, fatty aldehyde-caramel fragrance (alkaline preparation) fatty alcohol fragrance (acid preparation)

EXAMPLE 12

Mixture of 2-decyl-6-methyl-1,4-dioxane and 2-decyl-5-methyl-1,4-dioxane b.p.$_{0.05}$ 85° C. n$_D^{20}$ 1.447

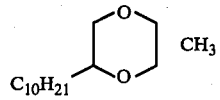

Odor: herbal, minty, fatty aldehyde fragrance (alkaline preparation) fresh, lumberjack fragrance (acid preparation)

EXAMPLE 13

10-methyl-9,12-dioxa-bicyclo-(6,4,0)-dodecane b.p.$_{0.2}$ 78° C. n$_D^{20}$ 1.4782

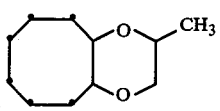

Odor: minty, anethole, herbal fragrance

EXAMPLE 14

9,12-dioxa-bicyclo-(6,4,0)-dodecane b.p.$_{0.1}$ 60° C. n$_D^{20}$ 1.4814

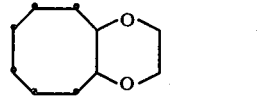

Odor: minty, potato fragrance

EXAMPLE 15

13,16-dioxa-bicyclo-(10,4,0)-hexadecane

Freezing point 79° C.

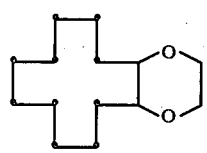

odor: earthy, camphoric, woody

All the compounds given in the above Examples have the described fragrances with excellent clinging properties or persistency which render them suitable for producing a wide variety of perfumery compositions. Such compositions can be used to perfume a wide variety of products such as cosmetics, washing agents, soaps as well as technical products in concentrations of approximately 0.05 to 2% by weight Examples of perfumery compositions having a content of the alkyl-substituted 1,4-dioxanes in accordance with the invention are given hereinafter.

EXAMPLE 16

| Cyclamen complex | Parts by Weight |
| --- | --- |
| 2-hexyl-5(6)-methyl-1,4-dioxane | 240 |

-continued

| Cyclamen complex | Parts by Weight |
|---|---|
| Hydroxycitronellal dimethylacetal | 300 |
| Nerol extra | 50 |
| L-citronellol | 50 |
| Cinnamic alcohol "Styrax" | 50 |
| αionone | 50 |
| αmethylionone | 50 |
| Bergamot oil | 50 |
| Lyral | 50 |
| Linalool | 40 |
| Rose rouge (Givaudan) | 30 |
| Jasmonis (Givaudan) | 20 |
| Anisic alcohol | 5 |
| Violet petals absolute 10% | 5 |
| Heliotropin | 5 |
| Rose oxide L (Dragoco) | 5 |
| | 1000 |

EXAMPLE 17

| Wood Base | Parts by Weight |
|---|---|
| 13,16-dioxa-bicyclo-(10,4,0)-hexadecane | 230 |
| Bergamot oil | 200 |
| α-iso-methylionone | 150 |
| Vetiveryl acetate | 100 |
| Cumarin | 60 |
| Santalol | 50 |
| Agar gel | 50 |
| Benzyl acetate | 30 |
| Cinnamyl acetate | 30 |
| Cedron S (IFF) | 20 |
| Ambrett musk | 20 |
| Bruyere Absolute (Robertet) | 20 |
| Gentiane Absolute (Robertet) | 15 |
| Peruvian balsam oil | 10 |
| Methyl-tetradecanolide | 10 |
| Caryophyllene alcohol | 5 |
| | 1000 |

EXAMPLE 18

| Aroma for mouth washes | Parts by Weight |
|---|---|
| 10-methyl-9,12-dioxa-bicyclo-(6,4,0)-dodecane | 100 |
| Peppermint oil, American, terpene-free | 500 |
| Anise oil | 200 |
| Methyl acetate | 85 |
| Star anise oil | 50 |
| Clove oil | 20 |
| Cinnamon oil | 15 |
| Carraway oil, terpene-free | 15 |
| Thyme Absolute | 5 |
| Ginger Absolute | 5 |
| Cyclopentane decanolide 1% | 5 |

| Aroma for mouth washes | Parts by Weight |
|---|---|
| | 1000 |

The preceding specific embodiments are illustrative of the practice of the invention. It is to be understood, however, that other expedients known to those skilled in the art or disclosed herein, may be employed without departing from the spirit of the invention or the scope of the appended claims.

We claim:
1. 10-Methyl-9,12-dioxa-bicyclo-(6,4,0)-dodecane.
2. 9,12-Dioxa-bicyclo-(6,4,0)-dodecane.
3. 13,16-Dioxa-bicyclo-(10,4,0)-hexadecane.
4. 10,11-Dimethyl-9,12-dioxa-bicyclo-(6,4,0)-dodecane.
5. 14-Methyl-13,16-dioxa-bicyclo-(10,4,0)-hexadecane.
6. 14,15-Dimethyl-13,16-dioxa-bicyclo-(10,4,0)-hexadecane.
7. A perfumery composition consisting essentially of from 1% to 50% by weight of the bicyclo-dodecane of claim 1, and the remainder customary constituents of perfumery compositions.
8. A perfumery composition consisting essentially of from 1% to 50% by weight of the bicyclo-dodecane of claim 2, and the remainder customary constituents of perfumery compositions.
9. A perfumery composition consisting essentially of from 1% to 50% by weight of the bicyclo-hexadecane of claim 3, and the remainder customary constituents of perfumery compositions.
10. A perfumery composition consisting essentially of from 1% to 50% by weight of the bicyclo-dodecane of claim 4, and the remainder customary constituents of perfumery compositions.
11. A perfumery composition consisting essentially of from 1% to 50% by weight of the bicyclo-hexadecane of claim 5, and the remainder customary constituents of perfumery compositions.
12. A perfumery composition consisting essentially of from 1% to 50% by weight of the bicyclo-hexadecane of claim 6, and the remainder customary constituents of perfumery compositions.
13. The perfumery composition of claim 7 wherein said customary constituents of perfumery composition include at least one other perfume.
14. The perfumery composition of claim 9 wherein said customary constituents of perfumery composition include at least one other perfume.

* * * * *